United States Patent

Howse

[11] Patent Number: 5,900,244
[45] Date of Patent: May 4, 1999

[54] INSECT ATTRACTANT

[75] Inventor: Philip Edwin Howse, Gosport, United Kingdom

[73] Assignee: University of Southampton, Southampton, United Kingdom

[21] Appl. No.: 08/677,979

[22] Filed: Jul. 10, 1996

[30] Foreign Application Priority Data

Jul. 20, 1995 [GB] United Kingdom ............. 9514873

[51] Int. Cl.⁶ .................................. A01N 25/10
[52] U.S. Cl. .................... 424/405; 424/408; 424/409; 424/410; 424/411; 424/195.1; 424/84; 514/699
[58] Field of Search ................ 424/84, 405, 406–410, 424/411, 195.1; 514/699

[56] References Cited

U.S. PATENT DOCUMENTS

| | | | |
|---|---|---|---|
| 3,996,349 | 12/1976 | Muller et al. ........................... | 424/84 |
| 4,600,581 | 7/1986 | Aldrich .................................. | 424/84 |
| 4,880,624 | 11/1989 | Metcalf et al. ........................ | 424/84 |
| 5,079,000 | 1/1992 | Takahashi et al. ................... | 424/195.1 |

FOREIGN PATENT DOCUMENTS

| | | |
|---|---|---|
| 7393723 | 8/1973 | Japan . |
| 56087511 | 7/1981 | Japan . |
| 06234602 | 8/1994 | Japan . |
| 1521413 | 8/1978 | United Kingdom . |

OTHER PUBLICATIONS

Leal et al —Kairomone from dandelion J. Chem. Ecol. 20 (7) 1697–704,1994.
Miles et al. Volatiles in Sarracenia Flava Phytochemistry vol. 14 1975 pp. 845–846.
Metcalf et al. J. Econ Entomology 82(6) 1989: 1620–5.
Gurnegs 1996 catalog —Venus fly Trap.
Copies of WPI Abstracts JP 50–42053, JP 51–79727, JP 56–87511, JP 59–62504 and JP 6–234602.
Phytochemistry (1975), 14(3), 845–6.
Chemical Abstracts, vol. 98, No. 3, 1983.
J. Econ. Entomol. (1989), 82(6), 1620–25.
Copy of GB Search Report for GB Application No. 9514873.0 dated Sep. 4, 1995.
Copy of PCT International Search Report for PCT/GB96/01736 dated Dec. 10, 1996.

*Primary Examiner*—Neil S. Levy
*Attorney, Agent, or Firm*—Fish & Richardson P.C.

[57] ABSTRACT

A method of attracting insects selected from the group consisting of houseflies, mosquitoes and wasps to a particular location, which method comprises placing at the said location a lure containing an effective attractant composition which comprises at least one compound which is a substituted benzenederivative having one or more short side chains, the said compound being volatile at room temperature and having a molecular weight in the range of from 115 to 155.

10 Claims, 2 Drawing Sheets

INSECT ATTRACTANT

BACKGROUND OF THE INVENTION

The present invention relates to an insect attractant and, in particular, to an insect attractant for houseflies, mosquitoes or wasps, which can be used to lure the insects to traps or other devices for the purpose of controlling such pests.

Insect attractants have been identified from food, from hosts or host plants of the insects themselves, from other insects (e.g. pheromones which are used in intraspecies chemical communication), and from the random screening of chemical compounds. Certain plants, including tropical pitcher plants (Nepenthes species), trumpet pitcher plants (Sarraceniaceae) and others capture insects and other animals which they are able to digest. The evidence which is summarised in Juniper,B. E., Robins,R. J., & Joel,D. M.(1989) The Carnivorous Plants, Academic Press suggests that the insects are attracted by visual stimuli (color patterns and reflected ultra violet light), and at close range are enticed to feed by the presence of viscous nectar secretions.

The volatile components in Sarracenia flava have been analysed by GC-MS analysis and the results are given in Phytochemistry, 1975, Vol.14, pp.845–846.

PRIOR ART

US-A-4880624 describes the use of compounds such a dimethoxybenzene, trimethoxybenzene or guaiacol admixed with one or more of indole, phenyl-acetaldehyde-hyde anethole, eugenol, cinnamaldehyde and cinnamoni-trile as attractants for the control of Diabrotica species of insects.

US-A-4600581 describes a synthetic pheromone composition for the spined soldier bug which comprises a mixture of a-terpineol, (E)-2-hexenal and benzyl alcohol.

JP-56087511 describes an insect attractant for pine tree borers, bark-beetles and wood-borers which comprises a lubricating oil, an antiseptic and an attracting compound such as salicylaldehyde, isobutyl salicylate, n-butyraldehyde, benzyl salicylate, isoamyl salicylate, benzaldehyde, phenylacetaldehyde, methylphenylketone or n-nonylaldehyde.

JP-A-59062504 describes as an attractant for the Hylemya species a composition comprising one or more of propionic acid, n-butyric acid, isobutyric acid, n-valeric acid, isovaleric acid, isocapronic acid and 2-phenylethanol.

JP-A-50042053 describes as an attractant for cockroaches compositions comprising aromatic compounds such as anisaldehyde, cinnamic aldehyde, heliotropin, acetophenone, methylionone, benzylacetone, benzyl alcohol, cinnamic alcohol, beta-phenylethyl alcohol, eugenol, sec-butylphenol, safrol, cinnamic acid, salicylic acid and phenylacetic acid.

Although the various prior art documents describe the use of certain compounds or mixtures of compounds which are attractive to particular defined species of insects, it is clear from the diversity of prior art that it is not possible to predict that any particular compound or mixture of compounds will be effective as an attractant for a particular insect species.

Accordingly, effective general purpose attractants that will lure a variety of insect species which are domestic pests, such as houseflies and mosquitoes, have not been described. Thus, while some food substances such as rotting meat will attract several species of flies, they will not usually attract other types of insects. Similarly floral odours will attract certain insect pollinators, such as bees and butterflies, but will not normally attract mosquitoes etc. It has therefore never been possible to attract more than a small variety of insects to any particular lure, and in the case of sexual pheromones usually only one species can be attracted.

We have now found that certain volatile chemical compounds, or mixtures of these compounds, can be used as insect attractants to trap houseflies, mosquitoes and wasps into a trap or onto a surface where they may be retained and killed.

SUMMARY OF THE INVENTION

Accordingly, the present invention provides a method of attracting houseflies, mosquitoes or wasps to a particular location, which method comprises placing at the said location a lure containing an effective attractant composition which comprises at least one compound which is a substituted benzene-derivative having one or more short side chains, which compound is volatile at room temperature and has a molecular weight in the range of from 115 to 155.

DETAILED DESCRIPTION OF THE INVENTION

Figure 1:
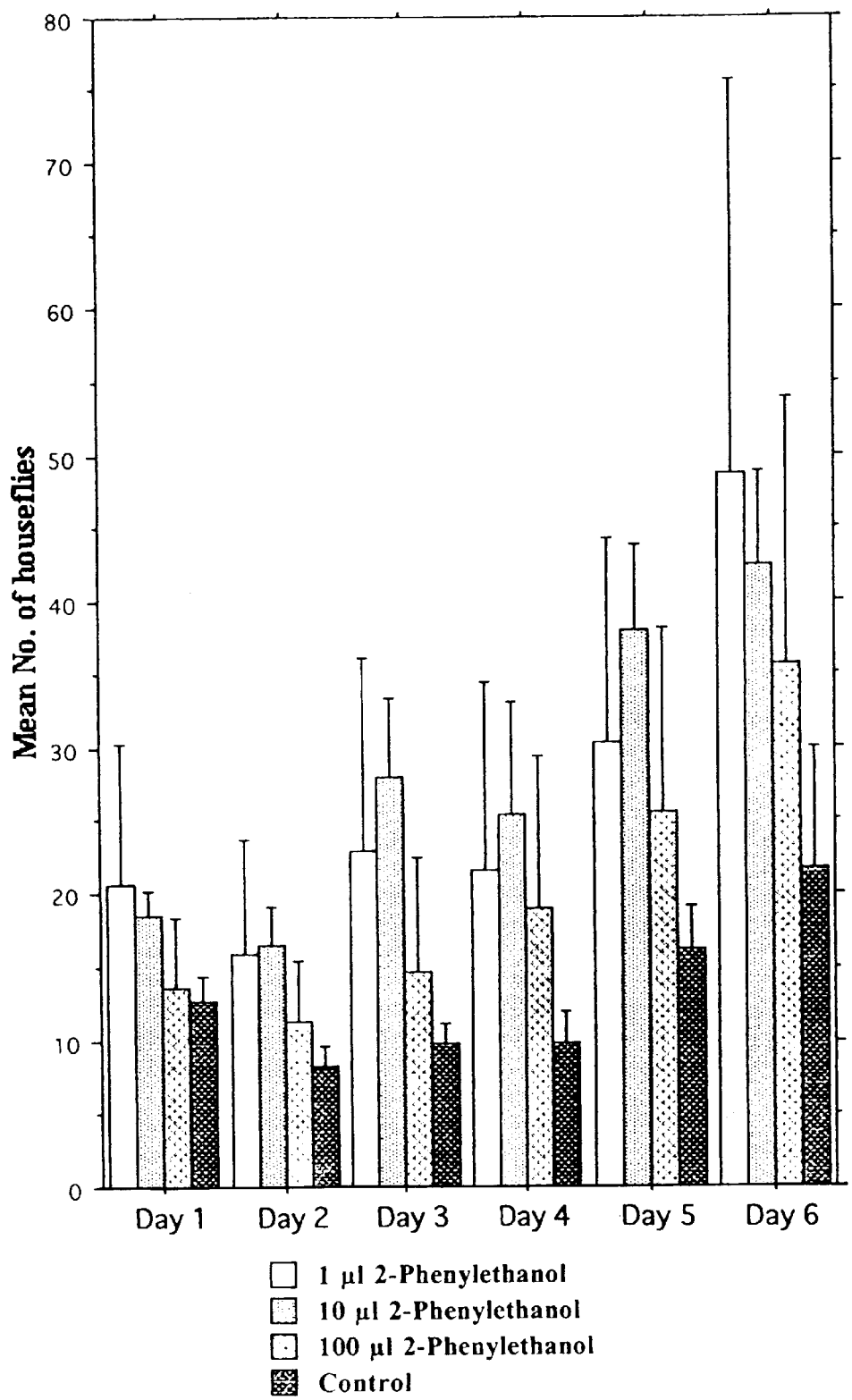
FIG. 1 illustrates the mean daily catch of houseflies in the experiment of Example 1.

The term "houseflies" is used herein to mean any flies that are commonly nuisances in the house and in particular *Musca domestica*, but also including house-flies sensu lato e.g. *Fannia cannicularis* (the lesser housefly) and Calliphora species (blowflies), or houseflies in the broad sense.

The attractant composition which is used in the method of the present invention comprises compounds which are naturally occurring and preferably comprises at least one of p-tolualdehyde, phenyl acetaldehyde, phenyl ethanol, phenyl ethylamine, benzyl acetate, benzyl alcohol, cinnamyl acetate or 3-phenyl-1-propanol.

Mixtures of compounds may also be used in the attractant compositions of the invention. Preferred mixtures for the attraction of common houseflies (*Musca domestics*) are phenyl ethanol and cinnamyl acetate, or phenyl ethanol and 3-phenyl-1-propanol, whilst for the attraction of blowflies (Calliphora) the preferred mixture is p-tolualdehyde with phenyl acetaldehyde.

The attractant compositions used in the method of the present invention may also comprise other optional ingredients such as carvacrol, fenugreek, sucrose, a sexual or aggregation pheromone, or an amine from protein decomposition.

The attractant compositions may, if desired, be derived from the secretions of carnivorous (insectivorous) plants such as species of Sarracenia, Nepenthes, Darlingtonia, Cephalotes or Heliamphora. These secretions are known to comprise a significant number of volatile constituents. For example, the secretions of *Sarracenia flava* have been found to contain at least 30 compounds including p-tolualde-hyde, 2-phenyl ethanol and carvacrol (Miles et al.(1975) Volatiles in *Sarracenia flava*, Phytochemistry 14, 845–846.

In order to ascertain whether a particular compound has an attractant effect on a particular insect, certain types of responses can be measured. Orientation towards a chemical source usually involves a sequence of behavioural patterns, including activation, take-off, directed up-wind flight, non-directed up-wind flight progression, landing on or near to the source and arrestance at the source. A given compound may elicit all or some only of these responses. The attraction to a chemical source may also be followed by feeding, or by sexual activity, or arrestance or by other behaviour. In some instances, and in particular in the case of sexual pheromones, the sequence of behaviour may be influenced by concentration such that a mixture of compounds that is attractant at one concentration is repellent at a higher concentration.

The insect attractant composition for use in the present invention is preferably formulated as a slow release composition, for example by being incorporated into hollow glass or fibre capillaries, or impregnated into porous polymeric substrates, cellulosic materials, rubber or wax.

The insect attractant compositions for use in the present invention may also be presented in combination with an insecticide, for example as an insect bait in microencapsulated form.

Alternatively, or in addition, the insect attractant composition may be placed inside an insect trap, or in the vicinity of the entrance to an insect trap. Insect traps which may be used are, for example, those as described in PCT/GB93/01442.

The present invention will be further described with reference to the following Examples.

EXAMPLE 1

The attraction of blowflies and houseflies to certain attractant compounds was tested in an olfactometer consisting of a wide-bore glass tube of internal diameter 9 cm and 90 cm long. The cylinder was sealed by a cotton mesh at each end and divided into three sections each 30 cm long. Filtered air was driven through the tube at 0.1 m/sec by an electric fan placed at one end of the tube. The central section was separated from the fan section by a mesh and the chemical under test was presented on a piece of cigarette filter placed just downwind of the fan. A line was drawn across the 30 cm central section to divide it into upwind and downwind halves. In each test 16 flies, 2 to 6 days old, were left in the cylinder for 4 hours (or two hours with the fan operating) in order to allow them to adjust to the experimental conditions prior to the introduction of the test compound. The control test lasted for 5 minutes prior to each test. The results are given in Tables 1 and 2 below:

TABLE 1

BLOWFLIES (Calliphora)

|  | Landings on upwind mesh/ 5 min | Take-offs/ min | Attempted feeding |
|---|---|---|---|
| Control 1 | 22 | 17 | — |
| p-Tolualdehyde | 41 | 5 | Some |
| Control 2 | 34 | 11 | — |
| p-Tolualdehyde | 48 | 17 | Some |
| Control 3 | 3 | 3 | — |
| Phenyl acetaldehyde | 16 | 35 | 16 |
| Control 4 | 0 | 14 | — |
| p-Tolualdehyde/ phenyl acetaldehyde/carvacrol | 14 | 119 | Frequent |
| Control 5 | 1 | 14 | — |
| p-Tolualdehyde phenylacetaldehyde/ carvacrol | 34 | 95 | Frequent |

TABLE 2

HOUSEFLIES (Musca domestica)

|  | Landings on upwind mesh/ 5 min | Take-offs/ min | Other Behaviour |
|---|---|---|---|
| Control 1 | 3 | 29 | — |
| Phenyl ethanol | 12 | 104 | Activation |
| Control 2 | 19 | 18 | — |
| Phenyl ethylamine | 12 | 47 | — |
| Control 3 | 5 | 4 | — |
| p-Tolualdehyde/phenyl acetaldehyde/ carvacrol | 32 | 10 | Mating/ feeding attempts |

EXAMPLE 2

Following the general procedure of Example 1 certain compounds were tested against blowflies at a temperature of 19 to 24° C. at a wind speed of 0.1 m/sec. The results are given in Table 3 below in the format: test (control).

TABLE 3

| Compound | Take-offs | Upwind displacement | Direct upwind flights | Landings on upwind mesh | Probing | Mating | Inhibition/ arrestant |
|---|---|---|---|---|---|---|---|
| 0.5 µl Tolualdehyde | 51 (2) | 11 (2) | — | 12 (0) | ++ (0) | — | — |
| 0.5 µl Phenyl acetaldehyde | 53 (6) | 11 (0) | 2 (0) | 11 (3) | + (0) | — | + (0) |
| 0.5 µl Carvacrol + 0.5 µl Tolualdehyde + 0.5 µl Phenyl acetaldehyde | 95 (14) | 34 (8) | 2 (0) | 21 (1) | — | — | — |

Where direct measurement was difficult, the number of bouts of probing with the proboscis or mating attempts was expressed on a scale where:
+ = 1 to 4
++ = 5 to 10
+++ = more than 10

EXAMPLE 3

Following the general procedure of Example 1 certain compounds were tested against houseflies at a temperature of 19 to 24° C. at a wind speed of 0.1 m/sec. The results are given in Table 4 below in the format: test (control).

TABLE 4

| Compound | Take-offs | Upwind displacement | Direct upwind flights | Landings on upwind mesh | Probing | Mating | Inhibition/arrestant |
|---|---|---|---|---|---|---|---|
| 0.5 µl Benzyl acetate | 85 (60) | 26 (11) | 4 (0) | 21 (21) | +++ (0) | ++ (++) | 0 (0) |
| 0.5 µl Benzyl alcohol | 65 (59) | 16 (11) | 1 (2) | 15 (8) | 0 (0) | + (++) | 0 (0) |
| 0.5 µl Cinnamyl acetate | 69 (56) | 18 (18) | 0 (2) | 7 (1) | 0 (0) | + (++) | 0 (0) |
|  | 51 (44) | 28 (21) | 1 (2) | 16 (9) | + (0) | ++ (+++) | 0 (0) |
| 0.5 µl 2-Phenyl ethanol | 104 (29) | 7 (2) | 0 (0) | 12 (3) | 0 (0) | — | after 8 minutes (0) |
|  | 129 (107) | 20 (25) | 6 (1) | 54 (22) | + (0) | +++ (+++) | after 5 minutes (0) |
| 0.5 µl 3-Phenyl-1-propanol | 114 (37) | 26 (20) | 0 (0) | 36 (24) | + (0) | ++ (+) | 0 (0) |
|  | 102 (91) | 14 (20) | 0 (0) | 22 (7) | +++ (0) | + (0) | 0 (0) |
| 0.5 µl (Z)-9-Tricosene (pheromone) | 45 (29) | 24 (23) | 1 (0) | 20 (21) | 0 (0) | + (+) | 0 (0) |
| 0.5 µl Carvacrol + 0.5 µl Tolualdehyde + 0.5 µl Phenyl acetaldehyde | 35 (34) | 10 (13) | 0 (0) | 20 (3) | 0 (0) | ++ (++) | 0 (0) |
| 0.5 ul Benzylacetate + 0.5 ul 2-Phenyl ethanol | 65 (25) | 7 (16) | 0 (0) | 14 (8) | 0 (0) | ++ (+) | ++ after 2.3 minutes (0) |

Where direct measurement was difficult, the number of bouts of probing with the proboscis or mating attempts was expressed on a scale where:
+ = 1 to 4
++ = 5 to 10
+++ = more than 10

EXAMPLE 4

One hundred houseflies, 2 to 6 days old, were placed in a standard fly test room, 29m³ in volume at a temperature of 26° C.±1° C.

The test room contained a box trap with black outer walls, 19 cm high×7.5 cm×7.5cm. Inner white cross vanes projected 1.5 cm out of the top of the open top of the box. The vanes were decorated with black spots to provide a visual attractant to encourage landing. The flies land on the vane which is coated with electrostatically charged particles of Carnauba wax as described in PCT/GB93/01442. When the flies land on the vanes they fall through downwardly projecting flaps into the base of the trap. The vanes were baited with a total of four 1 mm internal diameter glass capillaries charged with test compounds. The capillaries act to provide a controlled release of the test compound.

The captured flies were counted every hour for eight hours, from 11 am, and then at 24 hours.

The results are given in Table 5 below:

TABLE 5

| Test Substances | HOURS | | | | | | | | |
|---|---|---|---|---|---|---|---|---|---|
|  | 1 | 2 | 3 | 4 | 5 | 6 | 7 | 8 | 24 |
| Control - box trap without chemicals | 5 | 6 | 8 | 10 | 15 | 17 | 19 | 20 | 24 |
| Benzyl acetate | 3 | 6 | 8 | 23 | 27 | 32 | 33 | 34 | 43 |
| Benzyl alcohol | 3 | 5 | 12 | 14 | 18 | 20 | 27 | 29 | 44 |

TABLE 5-continued

| Test Substances | HOURS | | | | | | | | |
|---|---|---|---|---|---|---|---|---|---|
|  | 1 | 2 | 3 | 4 | 5 | 6 | 7 | 8 | 24 |
| Cinnamyl acetate | 3 | 8 | 15 | 25 | 34 | 35 | 37 | 43 | 51 |
| 2-Phenyl ethanol | 12 | 21 | 29 | 35 | 38 | 43 | 47 | 47 | 47 |
| 3-Phenyl-1-propanol | 3 | 10 | 22 | 25 | 29 | 33 | 35 | 36 | 40 |
| Tolualdehyde | 7 | 9 | 12 | 14 | 17 | 19 | 19 | 26 | 32 |
| (Z)-9-Tricosene + Sugar | 8 | 11 | 16 | 30 | 37 | 40 | 49 | 54 | 61 |

EXAMPLE 5

Following the general procedure of Example 1, certain compounds were tested against 15 female mosquitoes (*Aëdes aegypti*) at a temperature of 25° C. and at a windspeed of 0.1 m/sec. In these tests the candidate compounds were presented in a 1 mm diameter glass capillary and readings taken over a 15 minute period. The results are given in Table 6 below in the format: test (control).

TABLE 6

| Compounds | Take-offs | Landings on upwind mesh | Total flights | Direct upwind flights | Probing |
|---|---|---|---|---|---|
| Phenyl acetaldehyde | 24 (1) | 12 (0) | 49 (1) | 8 (0) | 1 (0) |

EXAMPLE 6

The efficacy of 2-phenyl ethanol as an attractant for houseflies was tested in a poultry rearing house 100 m×30 m.

Traps constructed from 1 ft×2 ft plywood boards were painted with a mixture of a contact insecticide (Alfacron$^R$) and sugar. There were 4 traps per treatment and 4 treatments. The treatments were as follows:

a) Control—a rubber septum was treated with sugar, the contact insecticide and dichloromethane solvent.

b) Tests A B and C—a rubber septum was treated with sugar, the contact insecticide and the following concentrations of 2-phenyl ethanol dissolved in dichloromethane solvent:
  A—1 µl 2-phenyl ethanol
  B—10 µl 2-phenyl ethanol
  C—100 µl 2-phenyl ethanol The rubber septa were used as substrates in order to control the emission rates of the 2-phenyl ethanol.

The catches were sampled by counting after 24 hours the contents of a bag placed at the base of the each trap. This was done on 6 separate days. The results of the experiments are shown in FIGS. 1 and 2.

FIG. 1 illustrates the mean daily catch of houseflies in traps containing the three concentrations of 2-phenyl ethanol and the control.

Figure 2:
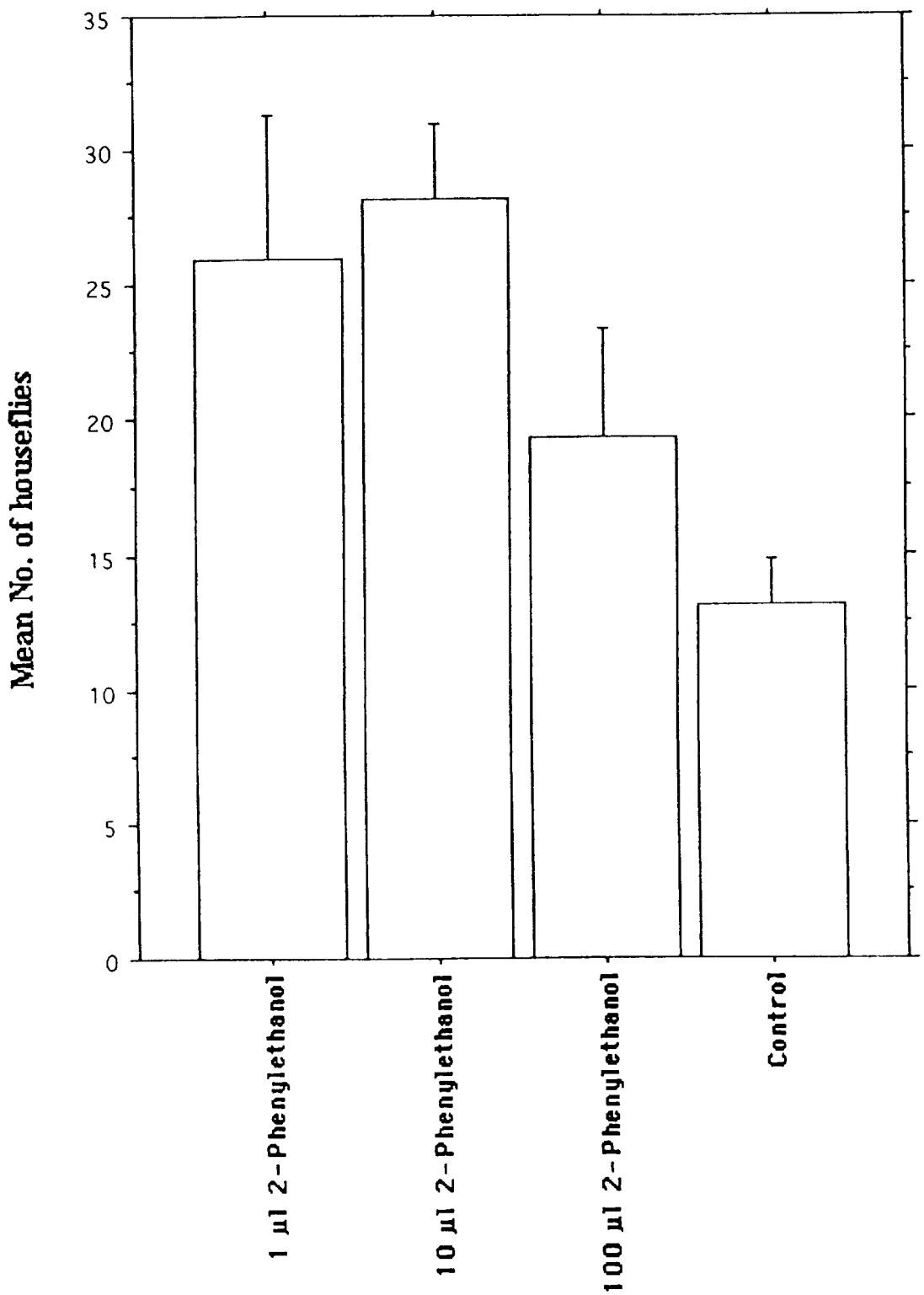
FIG. 2 illustrates the mean catch of houseflies in the experiment of Example 1.

FIG. 2 illustrates the mean catch of houseflies averaged over six days in traps containing the three concentrations of 2-phenyl ethanol and the control.

The results confirm that the 1 µl and 10 µl treatment catches were significantly different from the control catches. The 100 µl treatment catch was not as good as the 1 µl and 10 µl treatment catches, possibly because at the higher concentration 2-phenyl ethanol starts to exhibit an irritant effect.

I claim:

1. A method of attracting insects selected from the group consisting of houseflies, mosquitoes and wasps to a particular location, which method comprises placing at said location, a lure containing an effective amount, for the targeted insects, of an attractant composition which comprises phenyl acetaldehyde.

2. A method of attracting insects selected from the group consisting of houseflies, mosquitoes and wasps to a particular location, which method comprises placing at said location a lure containing an effective amount, for the targeted insects, of an attractant composition which comprises at least two compounds selected from the group consisting of p-tolualdehyde, phenyl acetaldehyde, phenyl ethanol, phenyl ethylamine, benzyl acetate, benzyl alcohol, cinnamyl acetate and 3-phenyl-1-propanol, said compounds being present in ratio to achieve effective attractant concentrations.

3. A method of attracting insects selected from the group consisting of houseflies, mosquitoes and wasps to a particular location, which method comprises placing at said location a lure containing an effective amount, for the targeted insects, of an attractant composition which comprises p-tolualdehyde.

4. A method according to claims 2, 3 or 1 wherein the composition additionally includes at least one compound selected from the group consisting of carvacrol, fenugreek, sucrose, a sexual or aggregation pheromone, and an amine from protein decomposition.

5. A method according to claims 2, 3 or 1 wherein the composition is derived from the secretions of carnivorous plants.

6. A method according to claim 5 wherein the carnivorous plant is a species of Sarracenia, Nepenthes, Darlingtonia, Cephalotes or Heliamphora.

7. A method according to claims 2, 3 or 1 wherein the attractant composition is placed inside an insect trap or in the vicinity of the entrance to an insect trap.

8. A method according to claims 2, 3 or 1 wherein the attractant composition is in the form of a slow release composition.

9. A method according to claims 2, 3 or 1 wherein the attractant composition is presented in combination with an insecticide.

10. A method according to claim 2 wherein the attractant composition is a composition for the attraction of houseflies and the compounds are selected from the group of mixtures consisting of phenyl ethanol plus cinnamyl acetate, phenyl ethanol plus 3-phenyl-1-propanol, and p-tolualdehyde plus phenyl acetaldehyde.

* * * * *